United States Patent
Babcock

(10) Patent No.: US 11,953,488 B2
(45) Date of Patent: Apr. 9, 2024

(54) SYSTEMS AND METHODS FOR DETERMINING CONCENTRATIONS OF MOBILE HYDROGEN OF METALLIC OBJECTS AND/OR REDUCING CONCENTRATIONS OF MOBILE HYDROGEN OF METALLIC OBJECTS

(71) Applicant: The Boeing Company, Chicago, IL (US)

(72) Inventor: Ed A. Babcock, Mesa, AZ (US)

(73) Assignee: THE BOEING COMPANY, Arlington, VA (US)

( * ) Notice: Subject to any disclaimer, the term of this patent is extended or adjusted under 35 U.S.C. 154(b) by 115 days.

(21) Appl. No.: 17/571,072

(22) Filed: Jan. 7, 2022

(65) Prior Publication Data

US 2022/0221439 A1    Jul. 14, 2022

Related U.S. Application Data

(60) Provisional application No. 63/137,006, filed on Jan. 13, 2021.

(51) Int. Cl.
*G01N 33/2025* (2019.01)
*G01N 1/22* (2006.01)
*G01N 1/44* (2006.01)

(52) U.S. Cl.
CPC ....... *G01N 33/2025* (2019.01); *G01N 1/2226* (2013.01); *G01N 1/44* (2013.01)

(58) Field of Classification Search
CPC .... G01N 33/2025; G01N 1/2226; G01N 1/44; G01N 1/02; G01N 2001/14; G01N 1/04

(Continued)

(56) References Cited

U.S. PATENT DOCUMENTS 3,426,579 A    2/1969    Lebel et al.
3,783,678 A    1/1974    Das et al.

FOREIGN PATENT DOCUMENTS

CN    107219296 A    *    9/2017    ............. G01N 1/286
WO    2018/056419    *    3/2018

OTHER PUBLICATIONS

Das, "An Ultrasensitive Hydrogen Detector", Hydrogen Embrittlement Testing, American Society for Testing and Materials ("ASTM"), ASTM Special Technical Publication 543, pp. 106-123 (1972).

(Continued)

*Primary Examiner* — Robert R Raevis
(74) *Attorney, Agent, or Firm* — MH2 Technology Law Group LLP

(57) ABSTRACT

An analytical inspection system for determining concentration of mobile hydrogen of and/or on surfaces of a metallic object can include: a vacuum furnace; a hydrogen sensing device; and/or a flow path from the furnace to the sensing device. The sensing device can be configured to detect and/or measure the mobile hydrogen at levels less than or equal to 1 part per million (ppm). An analytical inspection method for determining concentration of mobile hydrogen of and/or on surfaces of a metallic object can include: placing the object into a vacuum furnace; drawing a vacuum in the furnace; and/or simultaneously heating the metallic object in the furnace and measuring a quantity of the mobile hydrogen released from the object using a hydrogen sensing device. The sensing device can be configured to detect and/or measure the mobile hydrogen at levels less than or equal to 1 ppm.

37 Claims, 6 Drawing Sheets

(58) Field of Classification Search
USPC ... 73/19.01, 86, 87, 863.12, 863.81, 863.83, 73/866, 198; 374/45, 57; 422/68.1
See application file for complete search history.

(56) References Cited

OTHER PUBLICATIONS

Kowalewski et al., "Issues in Vacuum Brazing", Heat Treating Progress, May/Jun. 2006, pp. 41-45.

\* cited by examiner

SYSTEMS AND METHODS FOR DETERMINING CONCENTRATIONS OF MOBILE HYDROGEN OF METALLIC OBJECTS AND/OR REDUCING CONCENTRATIONS OF MOBILE HYDROGEN OF METALLIC OBJECTS

CROSS-REFERENCE TO RELATED APPLICATION(S)

This application claims the benefit of U.S. provisional patent application No. 63/137,006, filed on Jan. 13, 2021, in the U.S. Patent and Trademark Office ("USPTO"). The entire contents of the above application are incorporated herein by reference.

FIELD

The subject matter disclosed herein generally relates to systems and methods for determining concentrations of mobile hydrogen of metallic objects (e.g., in and/or on surfaces of the metallic objects). The subject matter disclosed herein also relates to systems and methods for reducing concentrations of mobile hydrogen of metallic objects (e.g., in and/or on surfaces of the metallic objects).

BACKGROUND

In many industries, such as the aerospace industry, significant reliance is placed on high strength steel ("HSS") and titanium alloys for critical applications. However, HSS and titanium alloys (and metals more generally) are susceptible to hydrogen embrittlement, which is a complex process that is not completely understood, but which can lead to sudden and/or severe failure of metallic components. Hydrogen embrittlement of metals can occur whenever and wherever metals are exposed to atomic or molecular hydrogen including, for example, various acids or water. The source of such exposure can be, for example, internal hydrogen embrittlement (e.g., carbonizing, casting, electroplating, heat treating, and/or welding) or hydrogen environmental embrittlement (e.g., galvanic corrosion, general corrosion, and/or exposure to chemicals or soils).

One example of internal hydrogen embrittlement is electroplating (e.g., with cadmium or zinc) of metallic components for corrosion protection. Because the electroplating process is not 100% efficient, some of the associated current applied goes into dissociation of water molecules ($H_2O$) into free hydrogen (e.g., H), hydrogen molecules ($H_2$), and oxygen molecules ($O_2$). Free hydrogen and/or hydrogen molecules generated on surfaces of the HSS and/or titanium alloys can be trapped in place, for example, by the deposition of metal ions on those surfaces during electroplating. If not removed, this free hydrogen (e.g., in ionic form) and/or hydrogen molecules can then diffuse interstitially into the HSS and/or titanium alloys and cause hydrogen embrittlement.

Some hydrogen in metallic components (whether or not electroplated) can be removed through the application of temperature over time. Hydrogen in metallic components that can be removed through the application of temperature over time, without melting the metallic components, is referred to as "mobile hydrogen".

Generally, in the application of temperature over time, as the time is increased, the temperature can be decreased and vice versa. However, in a manufacturing process, both time and temperature have associated costs, necessitating careful business, engineering, production, and other decisions.

A standard technique for reducing and/or removing such mobile hydrogen is to bake the electroplated metallic components in an air oven at high temperature (e.g., 375° F.) for a specified minimum period of time (e.g., 24 hours). For example, values of minimum baking time at 375° F. for different types of steels can be found in Heat Treatment of Steel Parts—General Requirements (AMS 2759).

This standard technique adds time and complexity, and increases costs associated with manufacturing of the electroplated metallic components. In addition, porosity of the electroplating affects the baking process because as plate porosity decreases, the efficiency of the baking process at removing mobile hydrogen also decreases.

Applicant notes that not all mobile hydrogen in metallic objects can be removed by such baking processes (e.g., nondestructive testing using heat for a specified minimum period of time). The mobile hydrogen that cannot be reduced or removed in this way can be removed by melting the metallic object. However, melting the metallic objects is a destructive testing method that can defeat the original purpose of the testing process.

For assessing the health of such metallic components with respect to hydrogen embrittlement (e.g., to ensure that the baking of the electroplated metallic components was effective), many industries, such as the aerospace industry, currently rely on periodic (e.g., weekly or monthly) testing of witness coupons that were electroplated in the same tanks as the metallic components, but not at the same time. Further, such witness coupons are electroplated only on a periodic basis, not with every batch of electroplated metallic components. As a result, the health of specific metallic components can only be inferred from the testing results of the witness coupons (e.g., witness coupons are only surrogates for the actual metallic components).

In addition, each test of witness coupons can take, for example, from 200 hours up to 10 days to complete (e.g., per the methodology of ASTM International F519—Standard Test Method for Mechanical Hydrogen Embrittlement Evaluation of Plating/Coating Processes and Service Environments). For this reason, production hardware is often released for use in manufacturing—with significant control, monetary, process, and other risks—pending completion of testing of the associated witness coupons.

Because of the issues discussed above, there is a need in many industries, such as the aerospace, automotive, defense, electronics, maritime, and rail-transport industries, for faster testing of such metallic components and for testing of the actual metallic components themselves, as opposed to the testing of witness coupons.

The disclosures of U.S. Pat. No. 3,426,579 to Lebel et al. ("Lebel") and U.S. Pat. No. 3,783,678 to Das et al. ("Das") are incorporated in the present application by reference.

SUMMARY

The present disclosure is directed to analytical inspection systems for determining concentration of mobile hydrogen of metallic objects (e.g., in and/or on surfaces of the metallic objects), analytical inspection methods for determining concentration of mobile hydrogen of metallic objects (e.g., in and/or on surfaces of the metallic objects), systems for reducing concentration of mobile hydrogen of metallic objects (e.g., in and/or on surfaces of the metallic objects), and/or methods for reducing concentration of mobile hydrogen of metallic objects (e.g., in and/or on surfaces of the metallic objects).

In some examples, an analytical inspection system for determining concentration of mobile hydrogen of a metallic object can comprise: a vacuum furnace; a hydrogen sensing device; and/or a flow path from the vacuum furnace to the hydrogen sensing device. The hydrogen sensing device can be configured to detect and/or measure the mobile hydrogen at levels less than or equal to 1 part per million (ppm).

In some examples of the analytical inspection system, the vacuum furnace can comprise a heating subsystem.

In some examples of the analytical inspection system, the vacuum furnace can comprise a cooling subsystem.

In some examples of the analytical inspection system, the vacuum furnace can comprise a carrier gas subsystem.

In some examples of the analytical inspection system, the vacuum furnace can comprise a pump subsystem configured to reduce pressure inside the vacuum furnace to less than about $1 \times 10^{-6}$ Torr.

In some examples of the analytical inspection system, the hydrogen sensing device can comprise a hydrogen detector or hydrogen analyzer.

In some examples of the analytical inspection system, the analytical inspection system can be configured to cause a flow of the mobile hydrogen out of the vacuum furnace in one direction.

In some examples of the analytical inspection system, the analytical inspection system can be configured to cause a flow of the mobile hydrogen out of the vacuum furnace in a first direction or in a second direction different from the first direction.

In some examples of the analytical inspection system, the hydrogen sensing device can comprise a mass spectrometer.

In some examples of the analytical inspection system, the metallic object can be an aerospace object.

In some examples of the analytical inspection system, the aerospace object can be an airplane part.

In some examples of the analytical inspection system, the vacuum furnace can comprise a pump subsystem configured to reduce pressure inside the vacuum furnace to less than about $1 \times 10^{-4}$ Torr and greater than about $1 \times 10^{-10}$ Torr.

In some examples of the analytical inspection system, the vacuum furnace can comprise a heating subsystem configured to raise temperature inside the vacuum furnace to greater than or equal to 100° F. and less than or equal to 1,000° F.

In some examples of the analytical inspection system, the vacuum furnace can comprise: a pump subsystem configured to reduce pressure inside the vacuum furnace to within a pressure band that is less than about $1 \times 10^{-4}$ Torr and greater than about $1 \times 10^{-10}$ Torr; and a heating subsystem configured to raise temperature inside the vacuum furnace to within a temperature band that is greater than or equal to 100° F. and less than or equal to 1,000° F. The pump subsystem and the heating subsystem can be configured to maintain the pressure band and the temperature band for greater than or equal to 0.5 hours and less than or equal to 50 hours.

An analytical inspection method for determining concentration of mobile hydrogen of a metallic object can comprise: placing the metallic object into a vacuum furnace; drawing a vacuum in the vacuum furnace; and/or simultaneously heating the metallic object in the vacuum furnace and measuring a quantity of the mobile hydrogen released from the metallic object using a hydrogen sensing device. The hydrogen sensing device can be configured to detect and/or measure the mobile hydrogen at levels less than or equal to 1 ppm.

In some examples of the analytical inspection method, measuring of the quantity of the mobile hydrogen released from the metallic object can comprise: drawing a sample from the vacuum furnace; and/or providing the sample to the hydrogen sensing device.

In some examples of the analytical inspection method, the hydrogen sensing device can comprise a hydrogen detector or hydrogen analyzer.

In some examples of the analytical inspection method, the analytical inspection method can cause a flow of the mobile hydrogen out of the vacuum furnace in one direction.

In some examples of the analytical inspection method, the analytical inspection method can cause a flow of the mobile hydrogen out of the vacuum furnace in a first direction or in a second direction different from the first direction.

In some examples of the analytical inspection method, the hydrogen sensing device can comprise a mass spectrometer.

In some examples of the analytical inspection method, the metallic object can be an aerospace object.

In some examples of the analytical inspection method, the aerospace object can be an airplane part.

In some examples of the analytical inspection method, the drawing of the vacuum in the vacuum furnace can comprise reducing pressure inside the vacuum furnace to less than about $1 \times 10^{-4}$ Torr and greater than about $1 \times 10^{-10}$ Torr.

In some examples of the analytical inspection method, the heating of the metallic object in the vacuum furnace can comprise raising temperature inside the vacuum furnace to greater than or equal to 100° F. and less than or equal to 1,000° F.

In some examples of the analytical inspection method, pressure inside the vacuum furnace can be reduced to within a pressure band that is less than about $1 \times 10^{-4}$ Torr and greater than about $1 \times 10^{-10}$ Torr, temperature inside the vacuum furnace can be raised to within a temperature band that is greater than or equal to 100° F. and less than or equal to 1,000° F., and/or the pressure band and the temperature band can be maintained for greater than or equal to 0.5 hours and less than or equal to 50 hours.

In some examples, a system for determining concentration of mobile hydrogen of a metallic object can comprise: a vacuum furnace; a hydrogen sensing device; and/or a flow path from the vacuum furnace to the hydrogen sensing device. The hydrogen sensing device can be configured to detect and/or measure the mobile hydrogen at levels less than or equal to 1 part per million (ppm).

In some examples of the system, the vacuum furnace can comprise a heating subsystem.

In some examples of the system, the vacuum furnace can comprise a cooling subsystem.

In some examples of the system, the vacuum furnace can comprise a carrier gas subsystem.

In some examples of the system, the vacuum furnace can comprise a pump subsystem configured to reduce pressure inside the vacuum furnace to less than about $1 \times 10^{-6}$ Torr.

In some examples of the system, the hydrogen sensing device can comprise a hydrogen detector or hydrogen analyzer.

In some examples of the system, the analytical inspection system can be configured to cause a flow of the mobile hydrogen out of the vacuum furnace in one direction.

In some examples of the system, the analytical inspection system can be configured to cause a flow of the mobile hydrogen out of the vacuum furnace in a first direction or in a second direction different from the first direction.

In some examples of the system, the hydrogen sensing device can comprise a mass spectrometer.

In some examples of the system, the metallic object can be an aerospace object.

In some examples of the system, the aerospace object can be an airplane part.

In some examples of the system, the vacuum furnace can comprise a pump subsystem configured to reduce pressure inside the vacuum furnace to less than about $1 \times 10^{-4}$ Torr and greater than about $1 \times 10^{-10}$ Torr.

In some examples of the system, the vacuum furnace can comprise a heating subsystem configured to raise temperature inside the vacuum furnace to greater than or equal to 100° F. and less than or equal to 1,000° F.

In some examples of the system, the vacuum furnace can comprise: a pump subsystem configured to reduce pressure inside the vacuum furnace to within a pressure band that is less than about $1 \times 10^{-4}$ Torr and greater than about $1 \times 10^{-10}$ Torr; and a heating subsystem configured to raise temperature inside the vacuum furnace to within a temperature band that is greater than or equal to 100° F. and less than or equal to 1,000° F. The pump subsystem and the heating subsystem can be configured to maintain the pressure band and the temperature band for greater than or equal to 0.5 hours and less than or equal to 50 hours.

In some examples, a method for reducing concentration of mobile hydrogen of a metallic object can comprise: placing the metallic object into a vacuum furnace; drawing a vacuum in the vacuum furnace; heating the metallic object in the vacuum furnace; measuring a quantity of the mobile hydrogen released from the metallic object using a hydrogen sensing device; and/or continuing the heating of the metallic object in the vacuum furnace until the measured quantity of the mobile hydrogen released from the metallic object is below a threshold value. The hydrogen sensing device can be configured to detect and/or measure the mobile hydrogen at levels less than or equal to 1 ppm.

In some examples of the method, the measuring of the quantity of the mobile hydrogen released from the metallic object can comprise: drawing a sample from the vacuum furnace; and/or providing the sample to the hydrogen sensing device.

In some examples of the method, the hydrogen sensing device can comprise a hydrogen detector or hydrogen analyzer.

In some examples of the method, the method can cause a flow of the mobile hydrogen out of the vacuum furnace in one direction.

In some examples of the method, the method can cause a flow of the mobile hydrogen out of the vacuum furnace in a first direction or in a second direction different from the first direction.

In some examples of the method, the hydrogen sensing device can comprise a mass spectrometer.

In some examples of the method, the metallic object can be an aerospace object.

In some examples of the method, the aerospace object can be an airplane part.

In some examples of the method, the drawing of the vacuum in the vacuum furnace can comprise reducing pressure inside the vacuum furnace to less than about $1 \times 10^{-4}$ Torr and greater than about $1 \times 10^{-10}$ Torr.

In some examples of the method, the heating of the metallic object in the vacuum furnace can comprise raising temperature inside the vacuum furnace to greater than or equal to 100° F. and less than or equal to 1,000° F.

In some examples of the method, pressure inside the vacuum furnace can be reduced to within a pressure band that is less than about $1 \times 10^{-4}$ Torr and greater than about $1 \times 10^{-10}$ Torr, temperature inside the vacuum furnace can be raised to within a temperature band that is greater than or equal to 100° F. and less than or equal to 1,000° F., and/or the pressure band and the temperature band can be maintained for greater than or equal to 0.5 hours and less than or equal to 50 hours.

In some examples of the method, the threshold value can be 1 ppm.

In some examples of the method, the heating of the metallic object in the vacuum furnace can be continued until the measured quantity of the mobile hydrogen released from the metallic object is reduced by 50%.

It is to be understood that both the foregoing general description and the following detailed description are exemplary and explanatory only, and are not restrictive of the present teachings, as claimed.

DRAWINGS

The above and/or other aspects and advantages will become more apparent and more readily appreciated from the following detailed description of examples, taken in conjunction with the accompanying drawings, in which.

Figure 5:
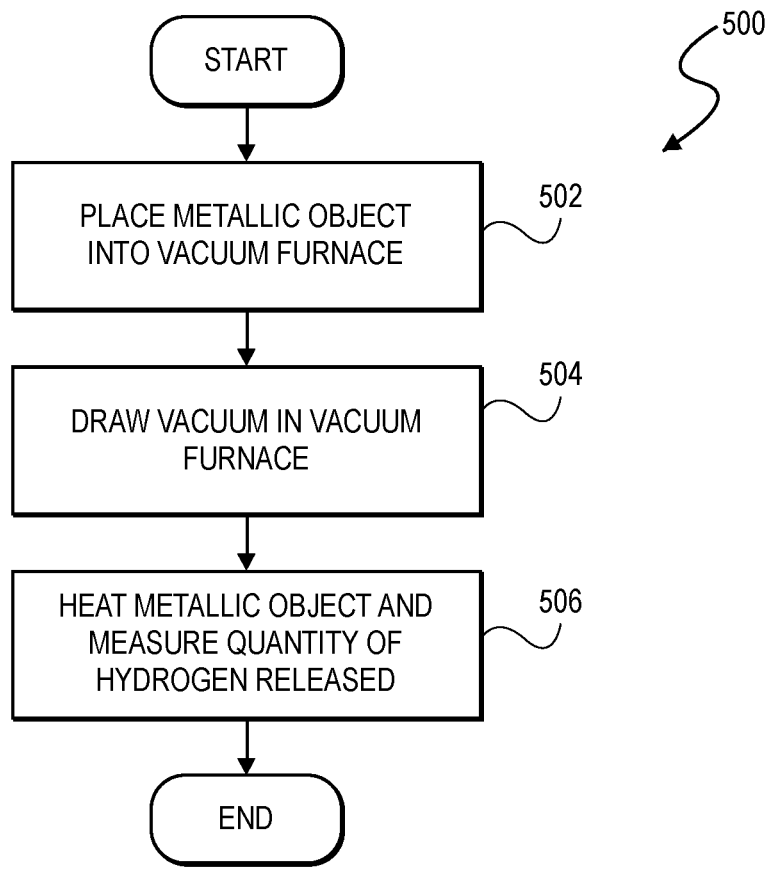
Figure 6:
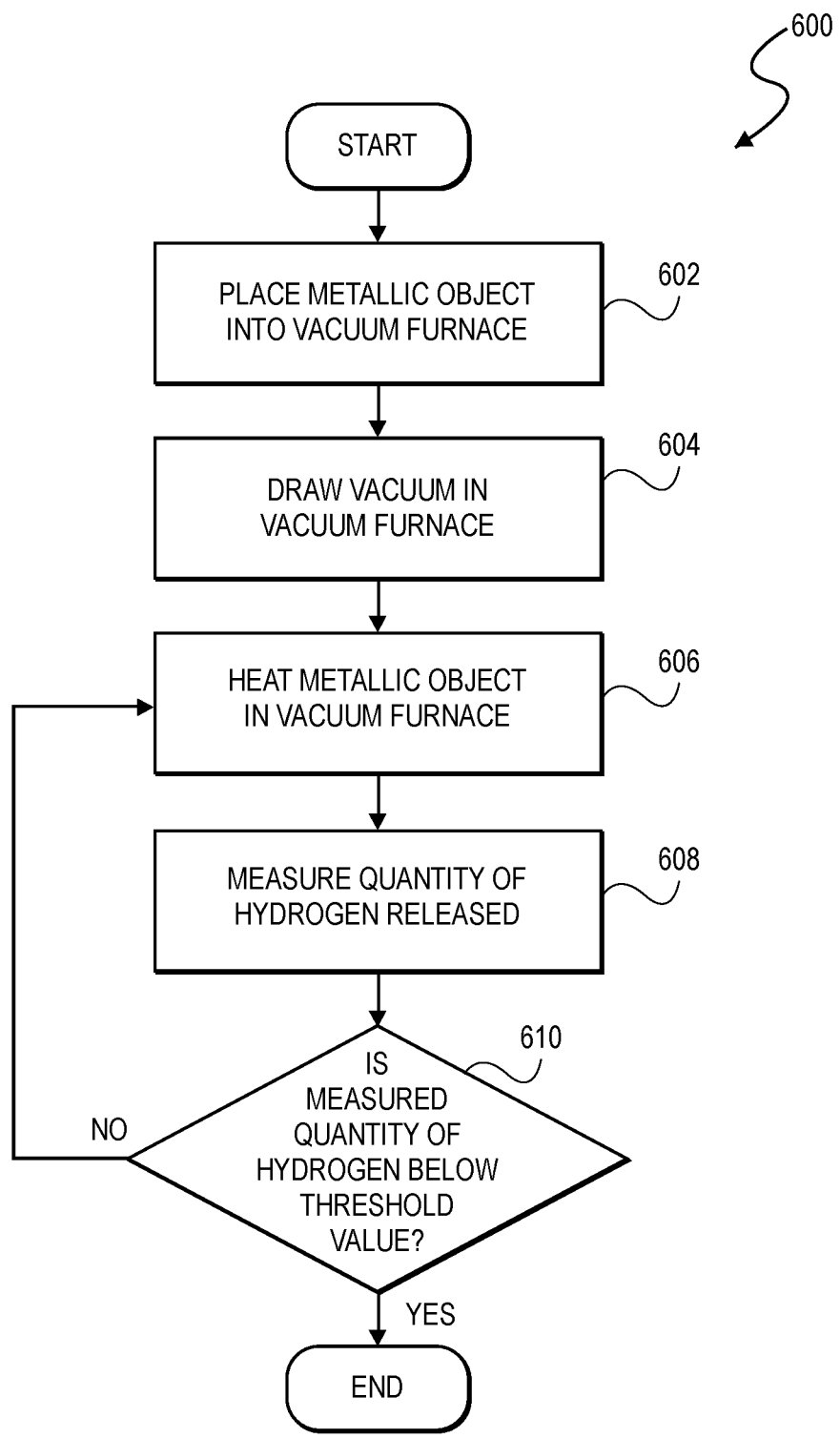

FIG. 5 shows an analytical inspection method for determining concentrations of mobile hydrogen of metallic objects (e.g., in and/or on surfaces of the metallic objects), according to some examples of the disclosed methods; and FIG. 6 shows a method for reducing concentration of mobile hydrogen of metallic objects (e.g., in and/or on surfaces of the metallic objects), according to some examples of the disclosed methods.

DETAILED DESCRIPTION

Exemplary aspects will now be described more fully with reference to the accompanying drawings. Examples of the disclosure, however, can be embodied in many different forms and should not be construed as being limited to the examples set forth herein. Rather, these examples are provided so that this disclosure will be thorough and complete, and will fully convey the scope to a person having ordinary skill in the art ("PHOSITA"). In the drawings, some details may be simplified and/or may be drawn to facilitate understanding rather than to maintain strict structural accuracy, detail, and/or scale. For example, the thicknesses of layers and regions may be exaggerated for clarity.

It will be understood that when an element is referred to as being "on," "connected to," "electrically connected to," or "coupled to" to another component, it may be directly on, connected to, electrically connected to, or coupled to the other component or intervening components may be present. In contrast, when a component is referred to as being "directly on," "directly connected to," "directly electrically connected to," or "directly coupled to" another component, there are no intervening components present. As used herein, the term "and/or" includes any and all combinations of one or more of the associated listed items.

It will be understood that although the terms first, second, third, etc., may be used herein to describe various elements, components, regions, layers, and/or sections, these elements, components, regions, layers, and/or sections should not be limited by these terms. These terms are only used to distinguish one element, component, region, layer, and/or section from another element, component, region, layer, and/or section. For example, a first element, component, region, layer, or section could be termed a second element, component, region, layer, or section without departing from the teachings of examples.

Spatially relative terms, such as "beneath," "below," "lower," "above," "upper," and the like may be used herein for ease of description to describe the relationship of one component and/or feature to another component and/or feature, or other component(s) and/or feature(s), as illustrated in the drawings. It will be understood that the spatially relative terms are intended to encompass different orientations of the device in use or operation in addition to the orientation(s) depicted in the figures.

The terminology used herein is for the purpose of describing particular examples only and is not intended to be limiting of examples. As used herein, the singular forms "a," "an," and "the" are intended to include the plural forms as well, unless the context clearly indicates otherwise. It will be further understood that the terms "comprises," "comprising," "includes," and/or "including," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as understood by a PHOSITA. It will be further understood that terms, such as those defined in commonly used dictionaries, should be interpreted as having a meaning that is consistent with their meaning in the context of the relevant art and should not be interpreted in an idealized or overly formal sense unless expressly so defined herein.

The present disclosure is directed to systems for determining concentrations of mobile hydrogen of metallic objects (e.g., in and/or on surfaces of the metallic objects).

Figure 1:
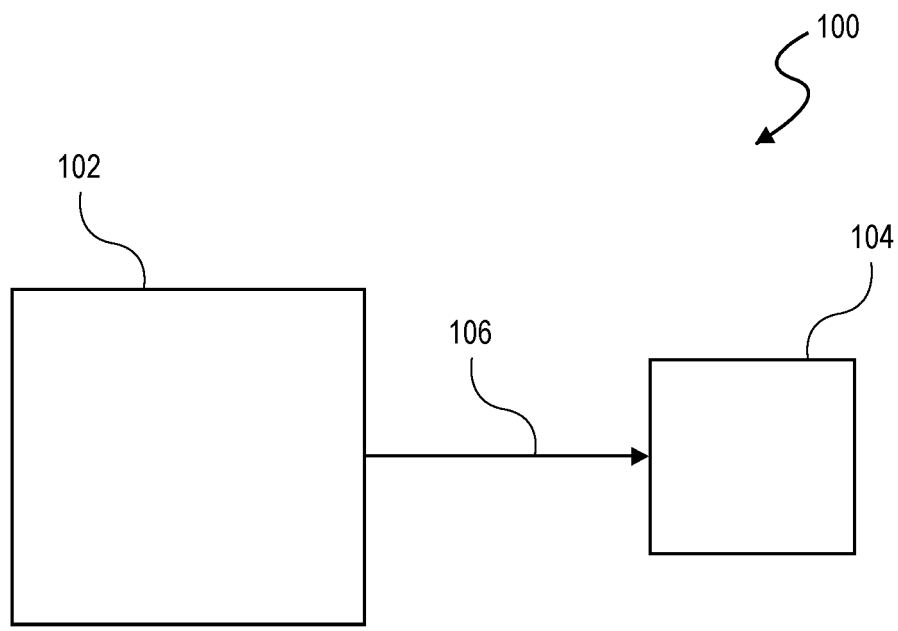
FIG. 1 shows an analytical inspection system for determining concentrations of mobile hydrogen of metallic objects (e.g., in and/or on surfaces of the metallic objects), according to some examples of the disclosed apparatuses.

FIG. 1 shows an analytical inspection system for determining concentrations of mobile hydrogen of metallic objects (e.g., in and/or on surfaces of the metallic objects), according to some examples of the disclosed apparatuses.

As shown in FIG. 1, analytical inspection system 100 can comprise: vacuum furnace 102; hydrogen sensing device 104; and/or flow path 106 from vacuum furnace 102 to hydrogen sensing device 104. Thus, analytical inspection system 100 is configured to cause a flow of mobile hydrogen out of vacuum furnace 102 in one direction.

Impetus for flow through analytical inspection system 100 is an overall pressure difference across analytical inspection system 100, with the highest pressure at vacuum furnace 102, pressure decreasing from vacuum furnace 102 toward hydrogen sensing device 104, and the lowest pressure at hydrogen sensing device 104. Such an overall pressure difference can be caused, for example, by one or more vacuum pumps (not shown) downstream from hydrogen sensing device 104. The one or more vacuum pumps can comprise, for example, one or more turbomolecular pumps.

One or more metallic objects can be placed into vacuum furnace 102, for example, immediately following the completion of an electroplating process. After placement of the one or more metallic objects into vacuum furnace 102, vacuum furnace 102 can be sealed and an initial vacuum drawn in vacuum furnace 102. While the initial vacuum is drawn, vacuum furnace 102 can be isolated, for example, from flow path 106 and hydrogen sensing device 104 by one or more valves (not shown).

The one or more metallic objects in vacuum furnace 102 simultaneously can be heated and a quantity of mobile hydrogen released from (e.g., desorbed from outer surfaces of) the one or more metallic objects. This quantity of mobile hydrogen released from and/or present on surfaces of the metallic object can be measured using hydrogen sensing device 104. Flow path 106 provides a route for the mobile hydrogen released from the one or more metallic objects to get from vacuum furnace 102 to hydrogen sensing device 104. Effectively, a stream of mobile hydrogen stripped from outer surfaces of the one or more metallic objects passes through hydrogen sensing device 104, where the mobile hydrogen is measured.

In some examples of the analytical inspection system, the hydrogen sensing device can comprise a hydrogen detector or hydrogen analyzer.

Hydrogen sensing device 104 can utilize one or more analytical techniques, such as electron capture, flame ionization, gas chromatography, mass spectrometry, or thermal conductivity. For example, hydrogen sensing device 104 can comprise a mass spectrometer. Such a mass spectrometer can use, for example, a previously developed correlation curve to determine the quantity of mobile hydrogen released from the metallic object based on the measurements made by the mass spectrometer. Such analytical techniques are known to a PHOSITA.

In some examples of analytical inspection system 100, hydrogen sensing device 104 is capable of detecting and/or measuring mobile hydrogen at levels less than or equal to 1 ppm, at levels less than or equal to 500 ppb, at levels less than or equal to 200 ppb, at levels less than or equal to 100 ppb, at levels less than or equal to 50 ppb, at levels less than or equal to 25 ppb, at levels less than or equal to 10 ppb, or at levels less than or equal to 5 ppb (e.g., 1 ppb). As such, the systems and methods of the present application represent a significant improvement over state-of-the-art hydrogen analyzers, at least some of which require exacting procedures for creating test specimens; which measure surface hydrogen, bulk hydrogen (e.g., hydrogen filled voids), and total hydrogen, but not mobile hydrogen, using the test specimens; and/or which destructively test (via melting) the test specimens.

Figure 2:
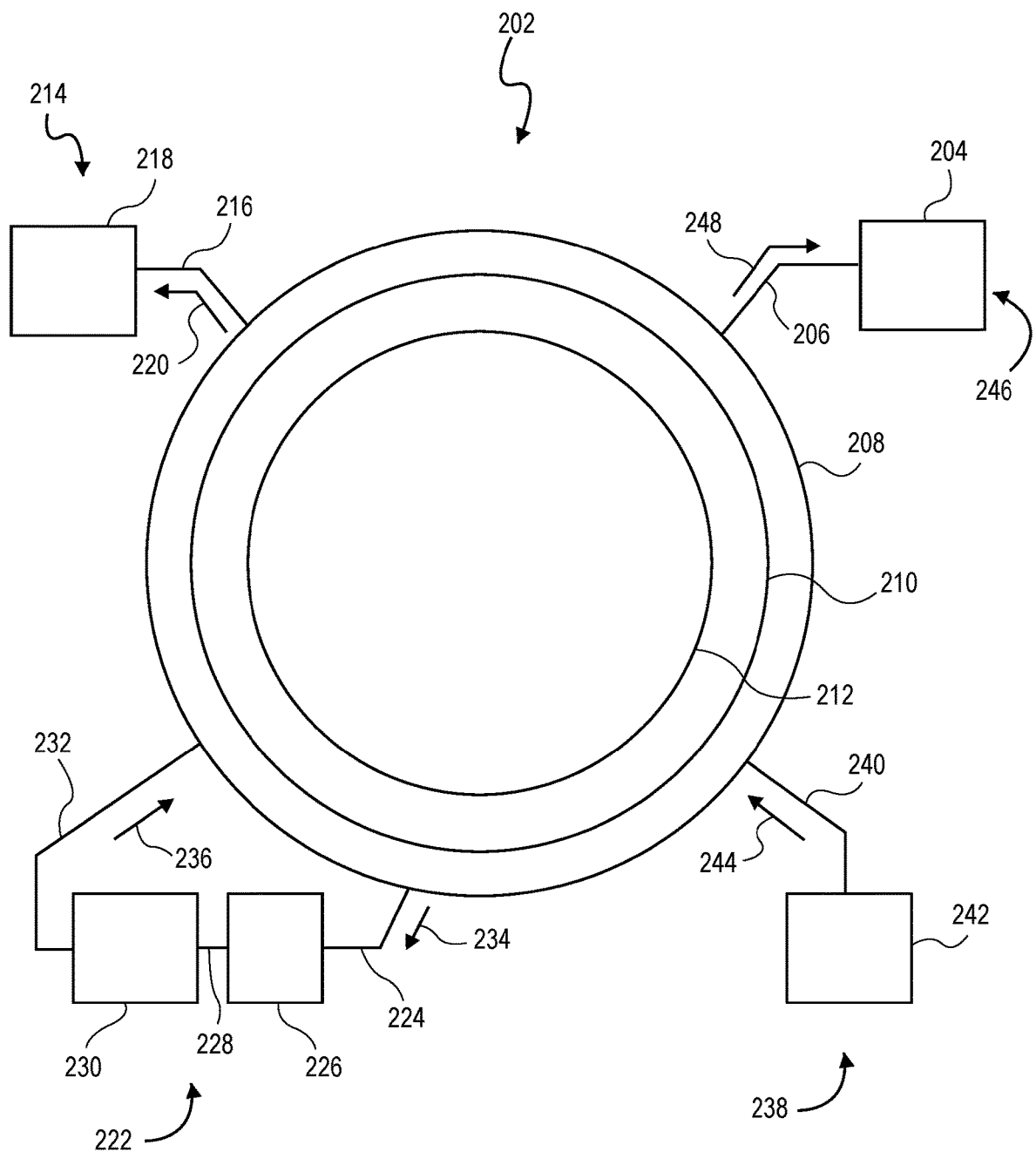
FIG. 2 shows a vacuum furnace, according to some examples of the disclosed apparatuses.

FIG. 2 shows a vacuum furnace, according to some examples of the disclosed apparatuses. As known to a PHOSITA, such a vacuum furnace can be, for example, a hot-wall design or a cold-wall design.

As shown in FIG. 2, vacuum furnace 202 can comprise: vacuum chamber 208; radiation shields/insulation 210; and/or heating subsystem 212. Vacuum furnace 202 can be connected to hydrogen sensing device 204 via flow path 206.

Vacuum chamber 208 can be, for example, a carbon steel or stainless steel cylindrical shell, typically closed at one end with an access door at the opposite end for loading/unloading of the one or more metallic objects and other uses (e.g., cleaning). The access door can comprise, for example, an autoclave-style locking ring.

Vacuum chamber 208 should be capable of withstanding significant pressure differences between an interior of vacuum chamber 208 and an exterior of vacuum chamber 208 (e.g., atmospheric pressure), whether the pressure is higher in the interior or higher on the exterior. Hence, vacuum chamber 208 can be of rugged design including, for example, thick-wall construction, double-wall construction, internal ribs, and/or external ribs. Because of this rugged design and associated multiple subsystems, vacuum chamber 208 typically costs much more (e.g., by a factor of about 10) than an air oven of comparable volumetric capacity.

Radiation shields/insulation 210 can define, for example, a hot zone associated with vacuum furnace 202. Effectively, the hot zone is the volume within radiation shields/insulation 210. The hot zone can be referred to, for example, as a graphite hot zone, in which radiation shields/insulation 210 typically comprise graphite (e.g., multiple layers of graphite felt), or an all-metal hot zone, in which radiation shields/insulation 210 typically comprise molybdenum and/or stainless steel (e.g., molybdenum and/or stainless steel sheet metal).

As design considerations, graphite is hygroscopic and graphite hot zones generally heat more slowly that all-metal hot zones.

Heating subsystem 212 can comprise, for example, electrical resistance heating elements comprising, for example, graphite, molybdenum, tantalum, and/or tungsten. In a graphite hot zone, the heating elements of heating subsystem 212 can comprise graphite. In an all-metal hot zone, the heating elements of heating subsystem 212 can comprise molybdenum.

Heating subsystem 212 can comprise, for example, a plurality of heating elements spaced circumferentially around vacuum chamber 208 and longitudinally down the length of vacuum chamber 208. For purposes of temperature uniformity within the hot zone, the heating elements of heating subsystem 212 can be spaced in a relatively uniform manner circumferentially and longitudinally.

As a design consideration, because graphite hot zones generally heat more slowly that all-metal hot zones, a graphite hot zone of heating subsystem 212 can require more heating elements and/or higher capacity heating elements than an all-metal hot zone.

The one or more metallic objects can be placed inside a volume generally defined by the heating elements of heating subsystem 212, inside of radiation shields/insulation 210, and inside of vacuum chamber 208.

Initially, the temperature in vacuum furnace 202, when vacuum furnace 202 is opened (e.g., to offload a previous batch of the one or more metallic objects and/or to load a subsequent batch of the one or more metallic objects), can be equal to ambient temperature. However, a PHOSITA would understand that during processing, when vacuum furnace 202 is opened, residual heat in vacuum furnace 202 can cause the temperature in vacuum furnace 202 to be higher than ambient temperature.

Initially, the pressure in vacuum furnace 202, when vacuum furnace 202 is opened, can be equal to ambient pressure. Once the one or more metallic objects are loaded into vacuum furnace 202, the access door can be closed and a vacuum drawn in vacuum furnace 202.

Generally, pressure at hydrogen sensing device 204 can be maintained at a vacuum (e.g., so that pressure $P_{hsd}$ at hydrogen sensing device 204 satisfies: $1\times10^{-10}$ Torr $\leq P_{hsd} \leq 1\times10^{-4}$ Torr, $1\times10^{-7}$ Torr $\leq P_{hsd} \leq 1\times10^{-5}$ Torr, or $1\times10^{-7}$ Torr $\leq P_{hsd} \leq 1\times10^{-6}$ Torr). While vacuum furnace 202 is opened (e.g., at ambient pressure), hydrogen sensing device 204 can be isolated using one or more isolation valves (not shown in FIG. 2).

Once the vacuum is drawn in vacuum furnace 202 such that the pressure in vacuum furnace 202 is approximately equal to the pressure at hydrogen sensing device 204, the one or more isolation valves can be opened.

During or after a vacuum is drawn in vacuum furnace 202, heating subsystem 212 can raise the temperature in vacuum furnace 202 to one or more temperatures within a range appropriate for the material of the one or more metallic objects. Thus, the time during which the vacuum has been drawn in vacuum furnace 202 is generally greater than or equal to the time during which heating subsystem 212 raises and maintains the temperature in vacuum furnace 202 within the range appropriate for the material of the one or more metallic objects.

For material of the one or more metallic objects comprising aluminum and/or aluminum alloys (aluminum alloyed with, for example, one or more of chromium, copper, iron, magnesium, manganese, silicon, titanium, vanadium, zinc, zirconium, or other element(s)), for example, the heating subsystems can raise the temperature in the vacuum furnace to greater than or equal to 77° F. and less than or equal to 1,200° F.; greater than or equal to 200° F. and less than or equal to 500° F.; or greater than or equal to 275° F. and less than or equal to 375° F.

For material of the one or more metallic objects comprising steels (iron and carbon alloyed with, for example, one or more of aluminum, boron, chromium, cobalt, copper, manganese, molybdenum, nickel, niobium, phosphorous, silicon, sulfur, titanium, tungsten, vanadium, zirconium, or other element(s)), for example, the heating subsystems can raise the temperature in the vacuum furnace to greater than or equal to 77° F. and less than or equal to 5,000° F.; greater than or equal to 100° F. and less than or equal to 1,000° F.; or greater than or equal to 250° F. and less than or equal to 550° F. For example, a temperature of about 285° F. could be appropriate for carburized low-alloy steels, while a temperature of about 500° F. could be appropriate for some high-hardness bearing steels.

For material of the one or more metallic objects comprising titanium and/or titanium alloys (titanium alloyed with, for example, one or more of aluminum, chromium, cobalt, copper, iron, manganese, molybdenum, nickel, niobium, nitrogen, oxygen, tantalum, vanadium, zirconium, or other element(s)), for example, the heating subsystems can raise the temperature in the vacuum furnace to greater than or equal to 77° F. and less than or equal to 3,000° F.; greater than or equal to 150° F. and less than or equal to 750° F.; or greater than or equal to 200° F. and less than or equal to 400° F.

Per Fick's laws of diffusion, raising the temperature of one or more metallic objects in the vacuum furnace will increase the diffusion of mobile hydrogen toward outer surfaces of the one or more metallic objects. This is particularly true because, during the heating, the vacuum furnace will be hotter than the one or more metallic objects. Thus, the one or more metallic objects will be hotter on outer surfaces than within the interior, so the driving force of the diffusion of mobile hydrogen will tend to favor diffusion toward the outer surfaces.

As also shown in FIG. 2, vacuum furnace 202 can further comprise: pump subsystem 214; cooling subsystem 222; optional carrier gas subsystem 238; and/or sampling subsystem 246.

As shown in FIG. 2, pump subsystem 214 can comprise first line 216 connecting vacuum chamber 208 to first vacuum pump 218. Generally, the direction of flow in first line 216 is defined by first arrow 220.

First vacuum pump 218 can comprise, for example, a cryopump, an ion-getter pump, a mechanical booster pump, a liquid sealing pump, an oil diffusion pump, a rotary pump, a titanium sublimation pump (e.g., with one or more titanium filaments), and/or a turbomolecular pump.

In order to quickly draw a strong vacuum in vacuum chamber 208, a motor associated with first vacuum pump 218 can be quite large (e.g., hundreds of horsepower or kilowatts).

As a design consideration, the capacity of first vacuum pump 218 can be driven by the size of vacuum chamber 208, the expected gas load when the initial vacuum is drawn, and/or the level of vacuum to be drawn in vacuum chamber 208.

As another design consideration, because graphite is hygroscopic, a graphite hot zone can require a more powerful first vacuum pump 218 than an all-metal hot zone.

In some examples of vacuum furnace 202, first vacuum pump 218 can lower the pressure inside vacuum chamber 208 to less than or equal to about $1\times10^{-3}$ Torr, less than or equal to about $1\times10^{-4}$ Torr, less than or equal to about $1\times10^{-5}$ Torr, less than or equal to about $1\times10^{-6}$ Torr, less than or equal to about $1\times10^{-7}$ Torr, less than or equal to about $1\times10^{-8}$ Torr, less than or equal to about $1\times10^{-9}$ Torr, less than or equal to about $1\times10^{-19}$ Torr, or less than or equal to about $1\times10^{-11}$ Torr (e.g., so that the pressure $P_s$ at the suction of first vacuum pump 218 satisfies: $1\times10^{-19}$ Torr$\leq P_s \leq 1\times10^{-4}$ Torr, $1\times10^{-7}$ Torr$\leq P_s \leq 1\times10^{-5}$ Torr, or $1\times10^{-7}$ Torr$\leq P_s \leq 1\times10^{-6}$ Torr). Such pressures can be measured, for example, by ionization gauges (not shown).

The time required for first vacuum pump 218 to lower the pressure inside vacuum chamber 208 depends, for example, on the interior volume of vacuum furnace 202 and associated piping, and the presence of flow restrictions (if any); on the type, size, and power of first vacuum pump 218; and on the desired pressure. The time required can be as short as five minutes or as long as an hour. Shorter or longer times can be envisioned depending upon circumstances (e.g., problems with continuity of power, system leaks, unusually large or small interior volume of vacuum furnace 202).

First vacuum pump 218 can remove air, oxygen, and other gases from the vacuum furnace. Such removal can reduce or prevent convective heat loss from one or more metallic objects in vacuum furnace 202, contamination of the one or more metallic objects, and/or oxidation of the one or more metallic objects.

As discussed above, a standard technique for removing mobile hydrogen from an electroplated metallic component is to bake the electroplated metallic component in an air oven at high temperature (e.g., 375° F.) for a specified minimum period of time (e.g., 24 hours). So, the baking by the air oven also takes advantage of Fick's laws of diffusion. However, in the air oven, the mobile hydrogen that diffuses to surfaces of the electroplated metallic component generally combines with oxygen molecules ($O_2$) in the air oven to form water molecules ($H_2O$), which is an exothermic reaction, and the water molecules subsequently evaporate due to the temperature in the air oven. Thus, there is a thermodynamic driving force behind the removal of this mobile hydrogen.

In contrast, in vacuum furnace 202, the mobile hydrogen that diffuses to surfaces of the electroplated metallic component is stripped away from those surfaces due to the vacuum in vacuum furnace 202. This vacuum-related driving force behind the removal of this mobile hydrogen is stronger than the thermodynamic driving force associated with the air oven. And the required time at temperature in vacuum furnace 202 can be significantly shorter than that for baking in an air oven. For example, the required time at temperature in vacuum furnace 202 can be greater than or equal to 15 minutes and less than or equal to about 150 hours (e.g., 100 hours), greater than or equal to 30 minutes and less than or equal to about 50 hours (e.g., 48 hours or 2 days), greater than or equal to 45 minutes and less than or equal to about 25 hours (e.g., 24 hours or 1 day), or greater than or equal to 1 hour and less than or equal to about 2 hours (e.g., 2 hours). For example, the required time at temperature in vacuum furnace 202 can be about 5 hours, about 4 hours, about 3 hours, about 2 hours, or about 1 hour. Thus, although the testing of witness coupons can take up to 200 hours, the present application can provide direct results from the one or more metallic objects in about 24 hours or fewer, and the results can be obtained during or after the one or more metallic objects is at pressure and temperature in vacuum furnace 202.

The systems and method of the present application can be used in tandem with hydrogen removal operations (e.g., a hydrogen-relief bake) or in a quality assurance process (e.g., after a hydrogen-relief bake). In addition, the systems and method of the present application can be used during Original Equipment Manufacturing ("OEM") or during overhaul/remanufacturing operations.

Therefore, the present application also provides systems and methods for reducing time at temperature requirements for reducing the hydrogen concentration of metallic objects. In addition, the present application provides systems and methods for increasing the efficiency and/or effectiveness of reducing hydrogen embrittlement in metallic objects.

Moreover, the present application eliminates the need for witness coupons in hydrogen embrittlement testing, and the associated problems with periodic testing of such witness coupons. Instead, the present application allows assessment of hydrogen-embrittlement-related data directly from the actual metallic objects for which such data is sought.

As shown in FIG. 2, cooling subsystem 222 can comprise second line 224 connecting vacuum chamber 208 to fan 226, third line 228 connecting fan 226 to heat exchanger 230, and fourth line 232 connecting heat exchanger 230 to vacuum chamber 208. Generally, the direction of flow in second line 224 is defined by second arrow 234, and the direction of flow in fourth line 232 is defined by third arrow 236.

In order to quickly cool vacuum chamber 208 and one or more metallic objects inside vacuum chamber 208, a motor associated with fan 226 can be quite large (e.g., hundreds of horsepower or kilowatts). As known to a PHOSITA, cooling subsystem 222 can shorten process cycle times and/or can act as a gas quench system.

In choosing a cooling gas, specific heat capacity and thermal conductivity of the gas can be important considerations. The cooling gas can comprise, for example, argon, helium, or nitrogen. In some examples, the cooling gas can be argon (optionally mixed with helium).

Although hydrogen is an acceptable cooling gas for some uses, it is not acceptable for the present application.

Gas pressure and gas velocity can be important in cooling subsystem 222, in which the only cooling mechanism can be convection. The gas pressure can be, for example, 1 bar (about 7.5×10² Torr) to 25 bar (about 1.9×10⁴ Torr), with the maximum pressure dependent upon the ruggedness of the design of vacuum chamber 208.

Fan 226 can drive the flow of the cooling gas in cooling subsystem 222. Heat exchanger 230 can be a direct gas-to-water heat exchanger.

As shown in FIG. 2, optional carrier gas subsystem 238 can comprise fifth line 240 connecting carrier gas supply 242 to vacuum chamber 208. Generally, the direction of flow in fifth line 240 is defined by fourth arrow 244.

The carrier gas can comprise, for example, argon, helium, or nitrogen. In some examples, the carrier gas can be helium.

Although hydrogen is an acceptable carrier gas for some uses, it is not acceptable for the present application.

When carrier gas is not used, mobile hydrogen released from the metallic object can leave vacuum chamber 208 via sampling subsystem 246. When carrier gas is used, mobile hydrogen released from the metallic object can be entrained in the carrier gas, the carrier gas with the entrained mobile hydrogen then leaves vacuum chamber 208 via sampling subsystem 246.

As shown in FIG. 2, sampling subsystem 246 can comprise flow path 206 connecting vacuum chamber 208 to hydrogen sensing device 204. Generally, the direction of flow in flow path 206 is defined by fifth arrow 248.

The relationship of vacuum furnace 202, hydrogen sensing device 204, and flow path 206 in sampling subsystem 246 can be similar to the relationship of vacuum furnace 102, hydrogen sensing device 104, and flow path 106 in analytical inspection system 100 of FIG. 1.

In some examples, hydrogen sensing device 204 is capable of detecting and/or measuring mobile hydrogen at levels less than or equal to 1 ppm, at levels less than or equal to 500 ppb, at levels less than or equal to 200 ppb, at levels less than or equal to 100 ppb, at levels less than or equal to 50 ppb, at levels less than or equal to 25 ppb, or at levels less than or equal to 10 ppb, or at levels less than or equal to 5 ppb (e.g., 2 ppb).

Figure 3:
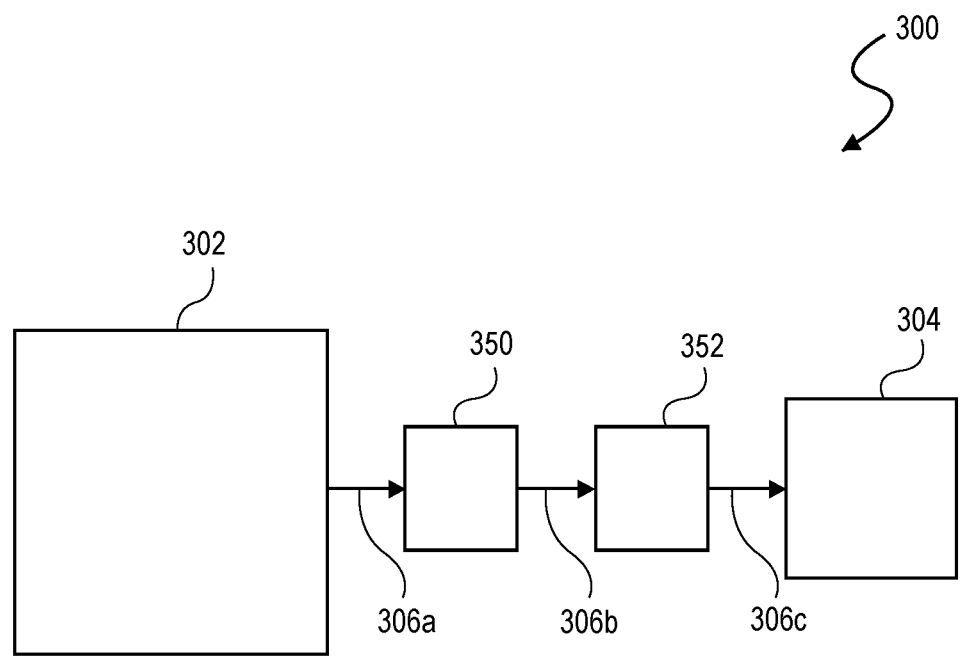
FIG. 3 shows an analytical inspection system for determining concentrations of mobile hydrogen of metallic objects (e.g., in and/or on surfaces of the metallic objects), according to some examples of the disclosed apparatuses.

FIG. 3 shows an analytical inspection system for determining concentrations of mobile hydrogen of metallic objects (e.g., in and/or on surfaces of the metallic objects), according to some examples of the disclosed apparatuses.

As shown in FIG. 3, analytical inspection system 300 can comprise: vacuum furnace 302; flow path 306a from vacuum furnace 302 to optional oxygen trap/oxygen scrubber solution subsystem 350; flow path 306b from optional oxygen trap/oxygen scrubber solution subsystem 350 to optional diffusion barrier subsystem 352; and flow path 306c from optional diffusion barrier subsystem 352 to hydrogen sensing device 304. Thus, analytical inspection system 300 is configured to cause a flow of mobile hydrogen out of vacuum chamber 302 in one direction.

Impetus for flow through analytical inspection system 300 is an overall pressure difference across analytical inspection system 300, with the highest pressure at vacuum furnace 302, pressure decreasing from vacuum furnace 302 toward hydrogen sensing device 304, and the lowest pressure at hydrogen sensing device 304. In particular, there can be a significant differential pressure across optional diffusion barrier subsystem 352. Such an overall pressure difference can be caused, for example, by one or more vacuum pumps (not shown) downstream from hydrogen sensing device 304. The one or more vacuum pumps can comprise, for example, one or more turbomolecular pumps.

In vacuum furnace 302, hydrogen can be present, for example, in elemental form, as water, and/or in organic material. Given the possibility for gases other than hydrogen to be present (e.g., argon, carbon dioxide, helium, krypton, neon, nitrogen, oxygen, and/or xenon), optional diffusion barrier subsystem 352 can serve as a permeable barrier specific for hydrogen only. Such a barrier can comprise, for example, a heated palladium or palladium-alloy (e.g., palladium-silver alloy or palladium-gold alloy) foil of small cross-sectional area (e.g., heated to about 1,100° F.). In the alternative, such a barrier can comprise a thin non-metallic membrane (e.g., ceramic or glass) as the barrier specific for hydrogen only. As would be understood by a PHOSITA, such a barrier can comprise, for example, one or more scrubbers for various chemical components (e.g., $CO_2$, $O_2$) and/or a molecular sieve column.

In addition, oxygen tends to react chemically with hydrogen in the presence of a hot metal surface (such as optional diffusion barrier subsystem 352) to form water, according to the following exothermic reaction.

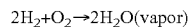

$$2H_2 + O_2 \rightarrow 2H_2O(vapor)$$

As a result, optional oxygen trap/oxygen scrubber solution subsystem 350 can remove such oxygen prior to optional diffusion barrier subsystem 352 so that the quantity of mobile hydrogen released from the metallic object is actually measured and not lost to water vapor.

In this way, optional oxygen trap/oxygen scrubber solution subsystem 350 can comprise a barrier specific for oxygen or oxygen only. Thus, optional oxygen trap/oxygen scrubber solution subsystem 350 can remove any gaseous oxygen from the flow that proceeds from vacuum furnace 302 to hydrogen sensing device 304.

Oxygen traps and oxygen scrubber solutions are known to a PHOSITA.

In some examples of the analytical inspection system, vacuum furnace 302 or the flow path from vacuum furnace 302 to hydrogen sensing device 304 can comprise optional diffusion barrier subsystem 352.

Optional diffusion barrier subsystem 352 can comprise a barrier specific for hydrogen only. Such a barrier can comprise, for example, heated palladium, heated palladium alloys (e.g., palladium-silver alloy or palladium-gold alloy), mild steel (e.g., low-carbon steel), nickel, or manganese alloys as the barrier specific for hydrogen only. The barrier can be in the form of a foil. In the alternative, such a barrier can comprise a thin non-metallic membrane (e.g., ceramic or glass) as the barrier specific for hydrogen only. As would be understood by a PHOSITA, such a barrier can comprise, for example, one or more scrubbers for various chemical components (e.g., $CO_2$, $O_2$) and/or a molecular sieve column.

Optional diffusion barrier subsystem 352 can remove any gases other than mobile hydrogen from the flow that proceeds from vacuum furnace 302 to hydrogen sensing device 304.

In some examples of analytical inspection system 300, hydrogen sensing device 304 is capable of detecting and/or measuring mobile hydrogen at levels less than or equal to 1 ppm, at levels less than or equal to 500 ppb, at levels less than or equal to 200 ppb, at levels less than or equal to 100 ppb, at levels less than or equal to 50 ppb, at levels less than or equal to 25 ppb, at levels less than or equal to 10 ppb, or at levels less than or equal to 5 ppb (e.g., 3 ppb).

Figure 4A:
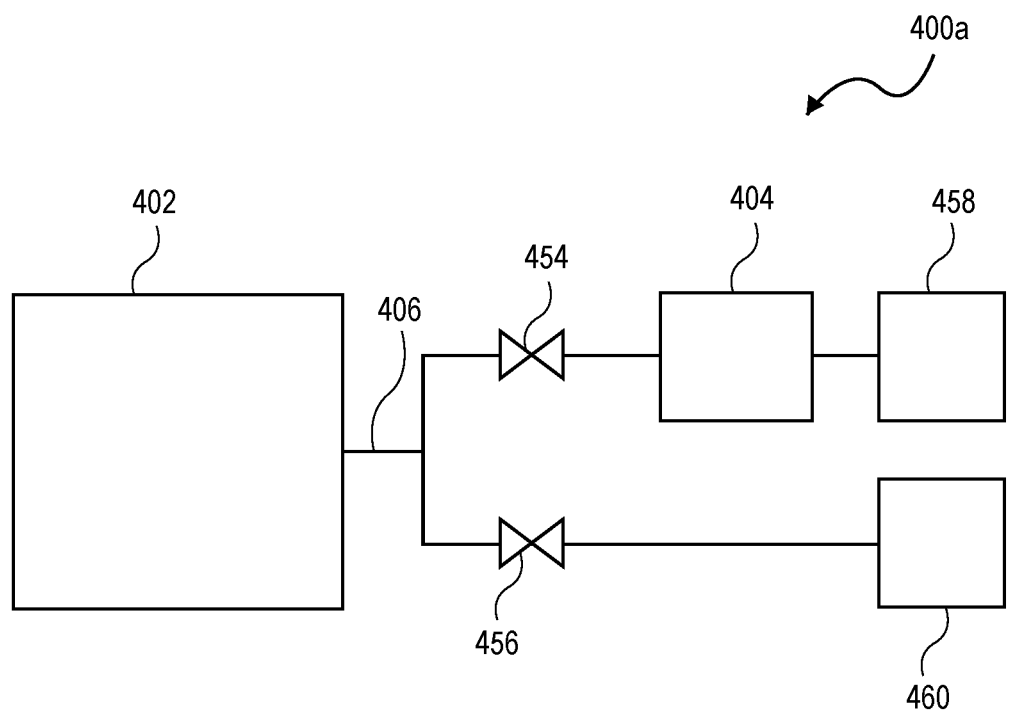
FIGS. 4A and 4B show analytical inspection systems for determining concentrations of mobile hydrogen of metallic objects (e.g., in and/or on surfaces of the metallic objects), according to some examples of the disclosed apparatuses.
Figure 4B:
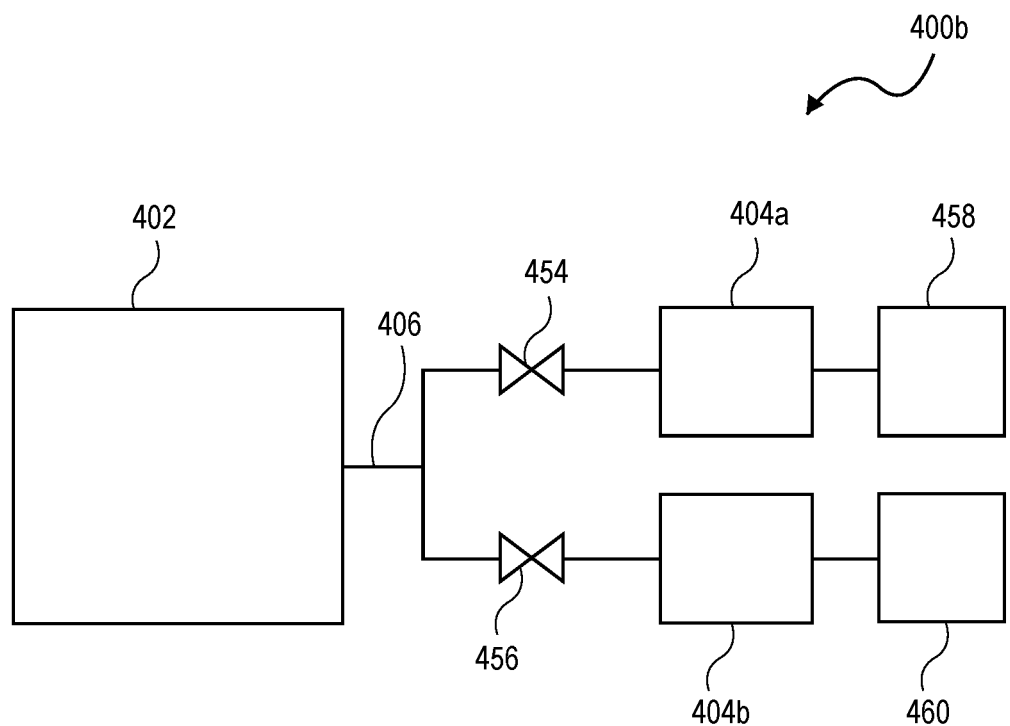

FIGS. 4A and 4B show analytical inspection systems for determining concentrations of mobile hydrogen of metallic objects (e.g., in and/or on surfaces of the metallic objects), according to some examples of the disclosed apparatuses.

As shown in FIG. 4A, analytical inspection system 400a can comprise: vacuum furnace 402; flow path 406 which splits (e.g., in a first direction) toward isolation valve 454, hydrogen sensing device 404, and second vacuum pump 458 and (e.g., in a second direction) toward isolation valve 456 and third vacuum pump 460. Thus, analytical inspection system 400a can be configured to cause a flow of mobile hydrogen out of vacuum furnace 402 in a first direction or in a second direction different from the first direction.

Second vacuum pump 458 and/or third vacuum pump 460 can comprise, for example, one or more cryopumps, ion-getter pumps, oil diffusion pumps (with cryogenic traps to minimize backstreaming of pump oil), titanium sublimation pumps, and/or turbomolecular pumps.

In some examples of analytical inspection system 400a, second vacuum pump 458 and/or third vacuum pump 460 can lower the pressure at a suction of the respective pump to less than or equal to about $1 \times 10^{-3}$ Torr, less than or equal to about $1 \times 10^{-4}$ Torr, less than or equal to about $1 \times 10^{-5}$ Torr, less than or equal to about $1 \times 10^{-6}$ Torr, less than or equal to about $1 \times 10^{-7}$ Torr, less than or equal to about $1 \times 10^{-8}$ Torr, less than or equal to about $1 \times 10^{-9}$ Torr, less than or equal to about $1 \times 10^{-10}$ Torr, or less than or equal to about $1 \times 10^{-11}$ Torr (e.g., so that the pressure $P_s$ at the suction of the respective pump satisfies: $1 \times 10^{-10}$ Torr$\leq P_s \leq 1 \times 10^{-4}$ Torr, $1 \times 10^{-7}$ Torr$\leq P_s \leq 1 \times 10^{-5}$ Torr, or $1 \times 10^{-7}$ Torr$\leq P_s \leq 1 \times 10^{-6}$ Torr). Such pressures can be measured, for example, by ionization gauges (not shown).

Analytical inspection system 400a can be operated with isolation valves 454 and 456 both shut. In this first mode, vacuum furnace 402 would be isolated and the associated first vacuum pump (e.g., similar to first vacuum pump 218 in FIG. 2), for example, could rapidly draw an initial vacuum in vacuum furnace 402.

Analytical inspection system 400a can be operated with isolation valve 454 open and isolation valve 456 shut. In this second mode, analytical inspection system 400a would operate similar to analytical inspection system 100 of FIG. 1, with second vacuum pump 458 reducing pressure at hydrogen sensing device 404 to provide the impetus for flow through analytical inspection system 400a.

Analytical inspection system 400a can be operated with isolation valve 454 shut and isolation valve 456 open. In this third mode, analytical inspection system 400a can be pumped down to an extremely low pressure to empty flow path 406 all the way back to vacuum furnace 402 in preparation for later operation.

In some examples of analytical inspection system 400a, hydrogen sensing device 404 is capable of detecting and/or measuring mobile hydrogen at levels less than or equal to 1 ppm, at levels less than or equal to 500 ppb, at levels less than or equal to 200 ppb, at levels less than or equal to 100 ppb, at levels less than or equal to 50 ppb, at levels less than or equal to 25 ppb, at levels less than or equal to 10 ppb, or at levels less than or equal to 5 ppb (e.g., 4 ppb).

As shown in FIG. 4B, analytical inspection system 400b can comprise: vacuum furnace 402; flow path 406 which splits (e.g., in a first direction) toward isolation valve 454, hydrogen sensing device 404a, and second vacuum pump 458 and (e.g., in a second direction) toward isolation valve 456, hydrogen sensing device 404b, and third vacuum pump 460. Thus, analytical inspection system 400b can be configured to cause a flow of mobile hydrogen out of vacuum furnace 402 in a first direction or in a second direction different from the first direction.

Hydrogen sensing device 404a and hydrogen sensing device 404b can be different devices, or analytical inspection system 400b can be designed with a single hydrogen sensing device that effectively can be switched back and forth between the position of hydrogen sensing device 404a and the position of hydrogen sensing device 404b. Either the two-device design or the switchable single-device design can provide significant advantages in flexibility over a single flow path design.

Second vacuum pump 458 and/or third vacuum pump 460 can comprise, for example, one or more cryopumps, ion-getter pumps, oil diffusion pumps (with cryogenic traps to minimize backstreaming of pump oil), titanium sublimation pumps, and/or turbomolecular pumps.

In some examples of analytical inspection system 400b, second vacuum pump 458 and/or third vacuum pump 460 can lower the pressure at a suction of the respective pump to less than or equal to about $1 \times 10^{-3}$ Torr, less than or equal to about $1 \times 10^{-4}$ Torr, less than or equal to about $1 \times 10^{-5}$ Torr, less than or equal to about $1 \times 10^{-6}$ Torr, less than or equal to about $1 \times 10^{-7}$ Torr, less than or equal to about $1 \times 10^{-8}$ Torr, less than or equal to about $1 \times 10^{-9}$ Torr, less than or equal to about $1 \times 10^{-10}$ Torr, or less than or equal to about $1 \times 10^{-11}$ Torr (e.g., so that pressure $P_s$ at the suction of the respective pump satisfies: $1 \times 10^{-19}$ Torr$\leq P_s \leq 1 \times 10^{-4}$ Torr, $1 \times 10^{-7}$ Torr$\leq P_s \leq 1 \times 10^{-5}$ Torr, or $1 \times 10^{-7}$ Torr$\leq P_s \leq 1 \times 10^{-6}$ Torr). Such pressures can be measured, for example, by ionization gauges (not shown).

Analytical inspection system 400b can be operated with isolation valves 454 and 456 both shut. In this first mode, vacuum furnace 402 would be isolated and the associated first vacuum pump (e.g., similar to first vacuum pump 218 in FIG. 2), for example, could rapidly draw an initial vacuum in vacuum furnace 402.

Analytical inspection system 400b can be operated with isolation valve 454 open and isolation valve 456 shut. In this second mode, analytical inspection system 400b would operate similar to analytical inspection system 100 of FIG. 1, with second vacuum pump 458 reducing pressure at hydrogen sensing device 404a to provide the impetus for flow through analytical inspection system 400b.

Analytical inspection system 400b can be operated with isolation valve 454 shut and isolation valve 456 open. In this third mode, analytical inspection system 400b would operate similar to analytical inspection system 100 of FIG. 1, with third vacuum pump 460 reducing pressure at hydrogen sensing device 404b to provide the impetus for flow through analytical inspection system 400b.

Switching between the second and third modes can allow for faster measurements of the hydrogen concentration of metallic objects in that the quantity of mobile hydrogen released from a first metallic object can be measured using the second mode, then the quantity of mobile hydrogen released from a second metallic object can be measured using the third mode, where the speed of measurements effectively can be reduced to the time required to switch from the first metallic object in the vacuum furnace at vacuum and temperature to the second metallic object in the vacuum furnace at vacuum and temperature.

Switching between the second and third modes also can allow for maintenance in the isolated flow path while operating the other flow path. The isolated flow path also can be pumped down to an extremely low pressure to empty that flow path back to the respective isolation valve in preparation for later operation.

In some examples of analytical inspection system 400b, hydrogen sensing device 404a is capable of detecting and/or measuring mobile hydrogen at levels less than or equal to 1 ppm, at levels less than or equal to 500 ppb, at levels less than or equal to 200 ppb, at levels less than or equal to 100 ppb, at levels less than or equal to 50 ppb, at levels less than or equal to 25 ppb, at levels less than or equal to 10 ppb, or at levels less than or equal to 5 ppb (e.g., 1, 2, 3, 4, or 5 ppb).

In some examples of analytical inspection system 400b, hydrogen sensing device 404b is capable of detecting and/or measuring mobile hydrogen at levels less than or equal to 1 ppm, at levels less than or equal to 500 ppb, at levels less than or equal to 200 ppb, at levels less than or equal to 100 ppb, at levels less than or equal to 50 ppb, at levels less than or equal to 25 ppb, at levels less than or equal to 10 ppb, or at levels less than or equal to 5 ppb (e.g., 1, 2, 3, 4, or 5 ppb).

FIG. 5 shows an analytical inspection method for determining concentrations of mobile hydrogen of metallic objects (e.g., in and/or on surfaces of the metallic objects), according to some examples of the disclosed methods.

As shown in FIG. 5, an analytical inspection method (500) for determining concentration of mobile hydrogen of a metallic object can comprise: placing the metallic object into a vacuum furnace (502); drawing a vacuum in the vacuum furnace (504), as discussed above; and simultaneously heating the metallic object and measuring a quantity of mobile hydrogen released from the metallic object using a hydrogen sensing device (506), as discussed above.

As used herein, "heating" a metallic object includes raising temperature inside the vacuum furnace, into which the metallic object has been placed, to a temperature band above ambient temperature and/or maintaining temperature inside the vacuum furnace, into which the metallic object has been placed, within a temperature band above ambient temperature.

The measuring of the quantity of mobile hydrogen released from the metallic object can comprise: drawing a sample from the vacuum furnace; and/or providing the sample to the hydrogen sensing device.

Drawing a sample from the vacuum furnace can comprise causing the sample to pass through an optional oxygen trap/oxygen scrubber solution subsystem and/or an optional diffusion barrier subsystem. As discussed above, the optional oxygen trap/oxygen scrubber solution subsystem reduces or eliminates oxygen gas from the sample, while the optional diffusion barrier subsystem selectively passes hydrogen in the sample.

Providing the sample to the hydrogen sensing device can comprise causing the sample to pass through an optional oxygen trap/oxygen scrubber solution subsystem and/or an optional diffusion barrier subsystem. As discussed above, the optional oxygen trap/oxygen scrubber solution subsystem reduces or eliminates oxygen gas from the sample, while the optional diffusion barrier subsystem selectively passes mobile hydrogen in the sample.

FIG. 6 shows a method for reducing concentration of mobile hydrogen of metallic objects (e.g., in and/or on surfaces of the metallic objects), according to some examples of the disclosed methods.

As shown in FIG. 6, a method (600) for reducing concentration of mobile hydrogen of a metallic object can comprise: placing the metallic object into a vacuum furnace (602); drawing a vacuum in the vacuum furnace (604), as discussed above; heating the metallic object in the vacuum furnace (606), as discussed above; measuring a quantity of mobile hydrogen released from the metallic object using a hydrogen sensing device (608), once at vacuum and temperature, such measurement can be virtually instantaneous and continuous; and continuing the heating of the metallic object in the vacuum furnace until the measured quantity of mobile hydrogen released from the metallic object is below a threshold value (610).

As discussed above, the measuring of the quantity of mobile hydrogen released from the metallic object using a hydrogen sensing device (608) can be virtually instantaneous and continuous. The mobile hydrogen measurement is real time, effectively being measured as fast as the mobile hydrogen comes out of the metallic object. Depending on thickness of the metallic object (which impacts the time required for diffusion), the measured quantity of the mobile hydrogen released from the metallic object can be below the threshold value (610) in as little as 2 hours or as long as 24 hours. Shorter or longer times can be envisioned depending upon circumstances (e.g., problems with continuity of power, system leaks, unusual geometry of the metallic object).

The heating of the metallic object in the vacuum furnace can be continued as required (e.g., until the measured quantity of the mobile hydrogen released from the metallic object is below a threshold value, until the measured quantity of the mobile hydrogen released from the metallic object is reduced by a specific percentage). For example, the heating of the metallic object in the vacuum furnace can be continued until the measured quantity of the mobile hydrogen released from the metallic object is below a threshold value, where the threshold value is 1 ppm, 500 ppb, 200 ppb, 100 ppb, 50 ppb, 25 ppb, 10 ppb, or 5 ppb. For example, the heating of the metallic object in the vacuum furnace can be continued until the measured quantity of the mobile hydrogen released from the metallic object is reduced by 50%, 60%, 70%, 75%, 80%, 90%, or 100%.

The systems and methods of the present application should reduce mobile hydrogen from a metallic object up to 100%. In addition, the systems and methods of the present application should significantly reduce (e.g., 50%) mobile hydrogen from a metallic object in as little as two hours, with reduction in mobile hydrogen potentially approaching 100% in as little as one or two days.

As also shown in FIG. 6, after heating the metallic object in the vacuum furnace (606) and measuring a quantity of mobile hydrogen released from the metallic object using a hydrogen sensing device (608), the measured quantity of mobile hydrogen released from the metallic object is compared to a threshold value (610). If the measured quantity of mobile hydrogen released from the metallic object is below the threshold value (610; YES), then the method ends. If the measured quantity of mobile hydrogen released from the metallic object is not below the threshold value (610; NO), then the heating of the metallic object in the vacuum furnace (606) and the measuring of the quantity of mobile hydrogen released from the metallic object using the hydrogen sensing device (608) continues until the measured quantity of mobile hydrogen released from the metallic object is below the threshold value (610; YES).

The measuring of the quantity of mobile hydrogen released from the metallic object can comprise: drawing a sample from the vacuum furnace; and/or providing the sample to the hydrogen sensing device.

Drawing a sample from the vacuum furnace can comprise causing the sample to pass through an optional oxygen trap/oxygen scrubber solution subsystem and/or an optional diffusion barrier subsystem. As discussed above, the optional oxygen trap/oxygen scrubber solution subsystem reduces or eliminates oxygen gas from the sample, while the optional diffusion barrier subsystem selectively passes hydrogen in the sample.

Providing the sample to the hydrogen sensing device can comprise causing the sample to pass through an optional oxygen trap/oxygen scrubber solution subsystem and/or an optional diffusion barrier subsystem. As discussed above, the optional oxygen trap/oxygen scrubber solution subsystem reduces or eliminates oxygen gas from the sample, while the optional diffusion barrier subsystem selectively passes mobile hydrogen in the sample.

In some examples of the analytical inspection system, the metallic object can be an aerospace, automotive, defense, electronics, maritime, or rail-transport object. In some examples of the analytical inspection system, the metallic object can be an aerospace object.

In some examples of the analytical inspection system, the aerospace object can be an aircraft, airplane, airship, drone, glider, helicopter, hot air balloon, lifting body, missile, rocket, rotorcraft, satellite, or spaceship part. In some examples of the analytical inspection system, the aerospace object can be an airplane part, such as one or more components of a landing gear.

Although examples have been shown and described in this specification and figures, it would be appreciated that changes can be made to the illustrated and/or described examples without departing from their principles and spirit, the scope of which is defined by the following claims and their equivalents.

What is claimed is:

1. An analytical inspection system for determining concentration of mobile hydrogen of a metallic object, the analytical inspection system comprising:
   a vacuum furnace receiving the metallic object, the metallic object being heated in the vacuum furnace;
   a hydrogen sensing device measuring a quantity of the mobile hydrogen released from the metallic object, the metallic object being heated until the measured quantity of the mobile hydrogen released from the metallic object is below a threshold value; and
   a flow path from the vacuum furnace to the hydrogen sensing device;
   wherein the hydrogen sensing device is configured to detect and/or measure the mobile hydrogen at levels less than or equal to 1 part per million (ppm).

2. The analytical inspection system of claim 1, wherein the vacuum furnace comprises a heating subsystem.

3. The analytical inspection system of claim 1, wherein the vacuum furnace comprises a cooling subsystem.

4. The analytical inspection system of claim 1, wherein the vacuum furnace comprises a carrier gas subsystem.

5. The analytical inspection system of claim 1, wherein the hydrogen sensing device comprises a hydrogen detector or hydrogen analyzer.

6. The analytical inspection system of claim 1, wherein the analytical inspection system is configured to cause a flow of the mobile hydrogen out of the vacuum furnace in one direction.

7. The analytical inspection system of claim 1, wherein the analytical inspection system is configured to cause a flow of the mobile hydrogen out of the vacuum furnace in a first direction or in a second direction different from the first direction.

8. The analytical inspection system of claim 1, wherein the hydrogen sensing device comprises a mass spectrometer.

9. The analytical inspection system of claim 1, wherein the metallic object is an aerospace object.

10. The analytical inspection system of claim 9, wherein the aerospace object is an airplane part.

11. The analytical inspection system of claim 1, wherein the vacuum furnace comprises a pump subsystem configured to reduce pressure inside the vacuum furnace to less than about $1 \times 10^{-4}$ Torr and greater than about $1 \times 10^{-10}$ Torr.

12. The analytical inspection system of claim 1, wherein the vacuum furnace comprises a heating subsystem configured to raise temperature inside the vacuum furnace to greater than or equal to 100° F. and less than or equal to 1,000° F.

13. The analytical inspection system of claim 1, wherein the vacuum furnace comprises:
   a pump subsystem configured to reduce pressure inside the vacuum furnace to within a pressure band that is less than about $1 \times 10^{-4}$ Torr and greater than about $1 \times 10^{-10}$ Torr; and
   a heating subsystem configured to raise temperature inside the vacuum furnace to within a temperature band that is greater than or equal to 100° F. and less than or equal to 1,000° F.;
   wherein the pump subsystem and the heating subsystem are configured to maintain the pressure band and the temperature band for greater than or equal to 0.5 hours and less than or equal to 50 hours.

14. An analytical inspection method for determining concentration of mobile hydrogen of a metallic object, the analytical inspection method comprising:
   placing the metallic object into a vacuum furnace;
   drawing a vacuum in the vacuum furnace;
   simultaneously:
      heating the metallic object in the vacuum furnace; and
      measuring a quantity of the mobile hydrogen released from the metallic object using a hydrogen sensing device; and
   continuing the heating of the metallic object in the vacuum furnace until the measured quantity of the mobile hydrogen released from the metallic object is below a threshold value;
   wherein the hydrogen sensing device is configured to detect and/or measure the mobile hydrogen at levels less than or equal to 1 part per million (ppm).

15. The analytical inspection method of claim 14, wherein the measuring of the quantity of the mobile hydrogen released from the metallic object comprises:
   drawing a sample from the vacuum furnace; and
   providing the sample to the hydrogen sensing device.

16. The analytical inspection method of claim 14, wherein the hydrogen sensing device comprises a hydrogen detector or hydrogen analyzer.

17. The analytical inspection method of claim 14, wherein the analytical inspection method causes a flow of the mobile hydrogen out of the vacuum furnace in one direction.

18. The analytical inspection method of claim 14, wherein the analytical inspection method causes a flow of the mobile hydrogen out of the vacuum furnace in a first direction or in a second direction different from the first direction.

19. The analytical inspection method of claim 14, wherein the hydrogen sensing device comprises a mass spectrometer.

20. The analytical inspection method of claim 14, wherein the metallic object is an aerospace object.

21. The analytical inspection method of claim 20, wherein the aerospace object is an airplane part.

22. The analytical inspection method of claim 14, wherein the drawing of the vacuum in the vacuum furnace comprises reducing pressure inside the vacuum furnace to less than about $1 \times 10^{-4}$ Torr and greater than about $1 \times 10^{-10}$ Torr.

23. The analytical inspection method of claim 14, wherein the heating of the metallic object in the vacuum furnace comprises raising temperature inside the vacuum furnace to greater than or equal to 100° F. and less than or equal to 1,000° F.

24. The analytical inspection method of claim 14, wherein pressure inside the vacuum furnace is reduced to within a pressure band that is less than about $1\times10^{-4}$ Torr and greater than about $1\times10^{-10}$ Torr,
  wherein temperature inside the vacuum furnace is raised to within a temperature band that is greater than or equal to 100° F. and less than or equal to 1,000° F., and
  wherein the pressure band and the temperature band are maintained for greater than or equal to 0.5 hours and less than or equal to 50 hours.

25. A method for reducing concentration of mobile hydrogen of a metallic object, the method comprising:
  placing the metallic object into a vacuum furnace;
  drawing a vacuum in the vacuum furnace;
  heating the metallic object in the vacuum furnace;
  measuring a quantity of the mobile hydrogen released from the metallic object using a hydrogen sensing device; and
  continuing the heating of the metallic object in the vacuum furnace until the measured quantity of the mobile hydrogen released from the metallic object is below a threshold value;
  wherein the hydrogen sensing device is configured to detect and/or measure the mobile hydrogen at levels less than or equal to 1 part per million (ppm).

26. The method of claim 25, wherein the measuring of the quantity of the mobile hydrogen released from the metallic object comprises:
  drawing a sample from the vacuum furnace; and
  providing the sample to the hydrogen sensing device.

27. The method of claim 25, wherein the hydrogen sensing device comprises a hydrogen detector or hydrogen analyzer.

28. The method of claim 25, wherein the method causes a flow of the mobile hydrogen out of the vacuum furnace in one direction.

29. The method of claim 25, wherein the method causes a flow of the mobile hydrogen out of the vacuum furnace in a first direction or in a second direction different from the first direction.

30. The method of claim 25, wherein the hydrogen sensing device comprises a mass spectrometer.

31. The method of claim 25, wherein the metallic object is an aerospace object.

32. The method of claim 31, wherein the aerospace object is an airplane part.

33. The method of claim 25, wherein the drawing of the vacuum in the vacuum furnace comprises reducing pressure inside the vacuum furnace to less than about $1\times10^{-4}$ Torr and greater than about $1\times10^{-10}$ Torr.

34. The method of claim 25, wherein the heating of the metallic object in the vacuum furnace comprises raising temperature inside the vacuum furnace to greater than or equal to 100° F. and less than or equal to 1,000° F.

35. The method of claim 25, wherein pressure inside the vacuum furnace is reduced to within a pressure band that is less than about $1\times10^{-4}$ Torr and greater than about $1\times10^{-10}$ Torr,
  wherein temperature inside the vacuum furnace is raised to within a temperature band that is greater than or equal to 100° F. and less than or equal to 1,000° F., and
  wherein the pressure band and the temperature band are maintained for greater than or equal to 0.5 hours and less than or equal to 50 hours.

36. The method of claim 25, wherein the threshold value is 1 ppm.

37. The method of claim 25, wherein the heating of the metallic object in the vacuum furnace is continued until the measured quantity of the mobile hydrogen released from the metallic object is reduced by 50%.

* * * * *